United States Patent
Birkenbach et al.

(10) Patent No.: US 8,328,793 B2
(45) Date of Patent: Dec. 11, 2012

(54) DEVICE, SYSTEM AND METHOD FOR INTEGRATING DIFFERENT MEDICALLY APPLICABLE APPARATUSES

(75) Inventors: Rainer Birkenbach, Poing (DE); Stefan Vilsmeier, Kufstein (AU)

(73) Assignee: Brainlab AG, Feldkirchen (DE)

( * ) Notice: Subject to any disclaimer, the term of this patent is extended or adjusted under 35 U.S.C. 154(b) by 965 days.

(21) Appl. No.: 10/715,962

(22) Filed: Nov. 18, 2003

(65) Prior Publication Data

US 2004/0116908 A1    Jun. 17, 2004

Related U.S. Application Data

(60) Provisional application No. 60/464,248, filed on Apr. 21, 2003.

(30) Foreign Application Priority Data

Dec. 13, 2002   (EP) ..................................... 02028015

(51) Int. Cl.
    *A61B 17/00*    (2006.01)
(52) U.S. Cl. .............................. 606/1; 600/101; 600/118
(58) Field of Classification Search ...... 606/1; 600/101, 600/118; 340/825
    See application file for complete search history.

(56) References Cited

U.S. PATENT DOCUMENTS

| | | | |
|---|---|---|---|
| 4,611,291 A * | 9/1986 | Hoelscher ........................ | 702/57 |
| 5,572,999 A * | 11/1996 | Funda et al. .................. | 600/118 |
| 5,788,688 A | 8/1998 | Bauer et al. | |
| 5,819,229 A * | 10/1998 | Boppe ............................... | 705/2 |
| 6,106,512 A * | 8/2000 | Cochran et al. ................... | 606/1 |
| 6,117,126 A | 9/2000 | Appelbaum et al. | |
| 6,117,127 A * | 9/2000 | Helmreich et al. ............... | 606/1 |
| 6,120,435 A * | 9/2000 | Eino .............................. | 600/118 |
| 6,397,286 B1 | 5/2002 | Chatenever et al. | |
| 6,471,363 B1 * | 10/2002 | Howell et al. .................... | 362/11 |
| 6,602,185 B1 * | 8/2003 | Uchikubo ...................... | 600/118 |
| 6,642,836 B1 * | 11/2003 | Wang et al. ................... | 340/3.54 |
| 6,659,939 B2 * | 12/2003 | Moll et al. ..................... | 600/102 |
| 6,824,539 B2 | 11/2004 | Novak | |
| 6,928,490 B1 | 8/2005 | Bucholz et al. | |

FOREIGN PATENT DOCUMENTS

WO    02/19957    3/2002

* cited by examiner

*Primary Examiner* — Matthew J Kasztejna

(74) *Attorney, Agent, or Firm* — Renner, Otto, Boissell & Sklar, LLP

(57) ABSTRACT

A device for coupling at least two medically applicable instruments, which are coupled to at least two control apparatuses, includes a central control unit coupled to input and/or output connections of said at least two control apparatuses. The central control unit includes at least one processor that receives output signals from the at least two control apparatuses and converts the output signals into a unified format. At least one processor receives inputted control signals, converts the control signals into formats corresponding to the respective at least two control apparatuses, and transfers the converted control signals to the at least two control apparatuses to control the at least two medically applicable instruments.

2 Claims, 1 Drawing Sheet

DEVICE, SYSTEM AND METHOD FOR INTEGRATING DIFFERENT MEDICALLY APPLICABLE APPARATUSES

RELATED APPLICATION DATA

This application claims priority of U.S. Provisional Application No. 60/464,248, filed on Apr. 21, 2003, which is incorporated herein by reference in its entirety.

FIELD OF THE INVENTION

The present invention relates generally to a device, a system and a method for integrating different medically applicable electric or electronic apparatuses. In particular, the invention relates to easily and cost-effectively integrating or interconnecting different apparatuses that control different devices, such as, for example, cameras, probes or pumps, and have, for example, different specifications at the interfaces for inputting and outputting data or control signals.

BACKGROUND OF THE INVENTION

In medical treatments, such as surgery, a multitude of different medical apparatuses having different functions are often used simultaneously. In open or minimally invasive surgery, for example, images can be recorded using laparoscopes and endoscopes. These devices can come from various manufacturers and display a respectively recorded image on a monitor also provided by the manufacturer, once the recording signals have been appropriately processed in corresponding control apparatuses or computational units obtained from the manufacturer. Furthermore, apparatuses for monitoring a patient's circulation or metabolism can be used during surgery to monitor the patient's condition before, during and after surgery and, as appropriate, to generate warning signals if, for example, the breathing or heartbeat show irregularities or if problems occur with the anaesthesia. Furthermore, depending on the type of surgery, fluoroscopy apparatuses, x-ray apparatuses, ultrasound apparatuses, nuclear spin tomographs etc. are used, with which images are generated, which are displayed on screens provided specially by the individual manufacturers. Depending on the equipment available, the patient table, the light, the volume of acoustic outputs or the room temperature, for example, can be adjusted differently by the surgeon. Workstations for surgery, in which various apparatuses are used, generally comprise a multitude of control devices belonging to the respective apparatus and a multitude of display instruments that a surgeon is often supposed to keep an eye on as simultaneously as possible during surgery.

A medico-technical system workstation for open or minimally invasive surgery is known from U.S. Pat. No. 6,117,127. This system includes a holder tray and at least one connecting unit for instruments of medico-technical apparatus, an apparatus center, which is spatially separated from the connecting unit, for recording the medico-technical apparatus and a coupling unit, which couples the connecting unit and the apparatus center to each other.

U.S. Pat. No. 6,471,363 B2 describes a device for surgical purposes that is attached to the ceiling of an operating theater and comprises various cameras and monitors, which can be pivoted relative to each other.

In the case of the known, so-called integrated systems for simultaneously operating a multitude of different apparatuses, the problem exists generally that either all the systems have to be obtained from a single manufacturer and thus apparatuses and systems such as may already be available cannot easily be integrated, or that different input and output specifications make integrating new apparatuses into a system more difficult, since manufacturer-specific protocols are used, such that the software has to be altered if one apparatus is to be interconnected with another, and since different manufacturers often choose different operating designs.

SUMMARY OF THE INVENTION

It is an object of the present invention to propose a device, a system and a method for integrating or coupling at least two or, in general, a plurality of medical apparatuses, which enables apparatuses with different specifications to be cost-effectively and easily integrated and interconnected.

In accordance with one embodiment, a device for coupling at least two or, alternatively, a plurality of medical electric or electronic apparatuses includes a central control unit to which the input and output connections of different control apparatuses of different medical instruments or apparatuses can be coupled. In this way, each medical apparatus, such as, for example, endoscopes, laparoscopes, pumps, ultrasound heads, drills, cameras or camera systems, and the like, can remain coupled to their respective control apparatus, such that it is not necessary to interfere with the internal running of the control systems of a medical apparatus. In other words, the software of a control apparatus for operating a medical instrument or apparatus does not have to be modified, such that no great costs are necessary for integrating a control apparatus for a medical instrument or apparatus into a system, neither with respect to the hardware nor with respect to the software.

In accordance with one embodiment of the invention, the input and output connections provided on the control apparatus of the individual medical instruments or apparatuses, for example, for connecting a keyboard, a cursor control device, such as a mouse, or a screen, are coupled to the central control unit. The central control unit can capture and further process only the data and/or signals necessary as an input and output interface to a user of the medical instrument or apparatus, in order, for example, to display data from one or more medical instruments or apparatuses on a single screen. Equally, a central input unit, such as, for example, a keyboard, a joystick, a mouse, a screen formed as a touch screen, a microphone for capturing speech signals, a hand-operated or foot-operated switch or the like, can be coupled to the central control unit, so as to capture signals or control information inputted by a user via the central control unit and to forward them to selected control apparatuses of the medical instruments or apparatuses, for example, in accordance with a selection made beforehand by the user, thus being able to change the adjustment or functionality of one or more medical instruments or apparatuses.

A video camera or camera system can also advantageously be provided, in order to transmit image data, for example, for video conferencing, or to store image data for documenting purposes. Such a camera can also be used, for example, as a webcam.

Only the signals of the control apparatus of the medical instruments that are necessary for interaction with a user are forwarded to the central control unit or forwarded from the central control unit to the individual control apparatus. Therefore, each individual apparatus can be used, without modifying the software or hardware, as it was designed to be by the respective manufacturer. The medical instrument coupled to the individual control apparatus can continue to be controlled as specified in the corresponding control apparatus by the manufacturer. In accordance with the invention, the display of images, signals or operational conditions of the medical instruments important for the user, such as output signals of the control apparatus, are detected by the central control unit and displayed on a central display, such as for example a flat screen. One or more control apparatuses, and therefore medical instruments, can be selected using a central input device and signals for determining or altering the operational mode or functionality can be transmitted on by the central input device to said control apparatus of the respective medical instruments via the central control unit.

In this way, the often large number of monitors and control apparatuses in the operating area, often having different operational designs, can be reduced. For example, a single monitor including a central input device for realizing a unified operational design can be realized. Different control apparatuses of different medical instruments can be controlled without, for example, rewriting the software used in the control apparatus or having to predetermine a special protocol for the manufacturer of a control apparatus, for communicating with the central control unit.

A unit for processing video signals of different formats can be provided in the central control unit. Using the processing unit, video signals of different formats for the monitors provided for the respective control apparatus can, for example, be processed and converted into a particular, selected video signal format, such that the video signals outputted by the different control apparatuses, possibly having different formats, can be displayed, for example, on a single monitor coupled to the central control unit. Methods and devices for converting video signals of a particular format into a different format, such as, for example, PAL to SECAM or other formats, are known in the prior art and will not be described in more detail here.

The connections for inputting control signals, provided on control apparatuses, are often standardized for connecting a commercially available keyboard, mouse, joystick, trackballs or the like and thus, in the event of standardized connections, can simply be coupled to the central control unit. A processor can also be provided in the central control unit, where the processor allows input signals of a particular format to be converted into a different format. The processor can, for example, be formed such that the signals inputted via a touch screen, on the keyboard displayed on the touch screen, are converted into control signals that are inputted to the keyboard connection of the control apparatus. Equally, the signals of different cursor control devices, such as, for example, mice, touch pads, joysticks, trackballs or the like, can be converted into other desired formats, such that, for example, an input apparatus coupled to the central control unit can generate control signals for moving a cursor. The control signals can be converted by a processor provided in the central control unit into control signals that can be interpreted by a particular control apparatus of a medical instrument, such that a unified operational design for operating different control apparatuses of different medical instruments can be realized, even though the control apparatus originally made it necessary, for example, to operate a first control apparatus using a keyboard, a second control apparatus using a mouse and a third control apparatus using a touch screen.

The device in accordance with the invention can be formed in the form of a cabinet or rack in which inserting drawers for two or more control apparatuses are provided. One, two or more control apparatuses inserted into the rack only have to be coupled to medical instruments controlled or operated by these control apparatuses. Additionally, coupling the control apparatuses to an operating theater is not necessary, since the inputs and outputs of the control apparatuses are guided via the central control unit, making it no longer necessary for a number of instruments to have to be provided at a surgical workstation, for outputting and inputting signals. Accordingly, the surgeon is not hindered in his work and is not confused due to the different operational designs. In addition, overall costs of a surgical workstation can be reduced, since apparatuses provided at such a workstation have to fulfil strict medical standards. By combining in a central display unit the input and output signals and the display of corresponding output signals, the overall costs of a surgical workstation can be significantly reduced. In general, the invention can even be used when the individual medical instruments are not coupled to each other spatially, for example, by a rack, as long as the principle of centrally capturing input and output signals of the individual control apparatuses is applied.

In one embodiment, the screen, touch screen, keyboard, mouse components or other input and output apparatus can be directly coupled to the central control unit, wherein it is possible for the respective components to respectively be coupled separately to the central control unit. In order to reduce the number of cables serving to couple the components, the corresponding signals can also be digitized, where these are not already in digital form, and can then be transmitted as a digital signal, for example, via an individual line used as bus, wherein at the end of the line, the digitally transmitted signals can be converted back into the original signals. Alternatively, it is also possible to wirelessly transmit a portion or all of the signals to be transmitted, such as, for example, by radio or infrared.

The at least one display device coupled to the central control unit and/or the at least one central input device for inputting control signals into the central control unit can also be coupled to the central control unit via a bus, for example, for transmitting data at a high data rate. The bus can be formed as an electrical cable, such as a coaxial cable, or as a glass fiber line, in order for safety reasons to separate electrically the central control unit and the control apparatus coupled to the control unit, on the one hand, and the apparatus situated in the surgeon's working environment, on the other hand, which is often desirable for safety reasons.

In accordance with another aspect, the invention relates to a system including a device as described above and a data output device and/or a data input device. The data output device can be, for example, a screen, such as a flat screen, which can also be formed as a touch screen and, therefore, also serve as a central input device. It is also possible to provide more than one data output device, wherein, for example, a large screen attached to the wall of an operating theater or room can be provided, in order, for example, to reproduce data or views, which can otherwise only be captured by a surgeon performing an operation or by a person operating an apparatus. The screen can, for example, be an LCD screen or can be based on plasma rear projection or frontal projection. In general, any display apparatus which is suitable for use in the area of medicine can be used in accordance with the invention. On the basis of medical standards, it can, for example, be stipulated in this respect that the display device can be operated sterilely.

The input device for inputting control signals can also be designed in accordance with the requirements of a sterile working environment. For example, it should be possible for a surgeon wearing gloves to select particular options or menus and to input corresponding operational or control commands. In this respect, a screen provided as a display can be formed as a touch screen, such that different menus can be selected and displayed on the screen and a surgeon can select a particular medical instrument and/or the corresponding control apparatus and can make particular adjustments to it simply by touching a corresponding field displayed on the screen.

A storage unit can be provided, in which a selected portion or all of the signals outputted by the medical instruments coupled to the central control unit are stored. Furthermore, all the adjustments or inputs made by the user can also be stored in the storage unit, in order to have corresponding data available, for example, for teaching purposes or for documenting a surgical operation.

In one embodiment, at least one of the components or devices forming the system in accordance with the invention is mounted on the ceiling of an operating theater or room. A device for optically capturing data, such as, for example, a camera, a magnifying device, holding devices for medical instruments, screens, such as, for example, a touch screen, data input devices such as, for example, a keyboard, a joystick or other components can be directly mounted to the ceiling or attached to or held by supports mounted to the ceiling. In one embodiment, apparatuses or instruments mounted on the ceiling can be moved, to which end pivoting and/or rotating arms with one or more joints can be provided. Mounting on the ceiling reduces the floor space required in the operating theater and thus leads to an improvement in mobility for persons moving in the operating theater or apparatus or instruments to be moved or relocated on the floor.

In accordance with another aspect, the invention relates to a method for operating at least two medical instruments or apparatuses simultaneously, in parallel or sequentially, wherein the output signals of the medical instruments or of the control apparatuses coupled to the medical instruments are transmitted to a central control unit. The control unit can transmit input signals to the medical instruments or the control apparatuses coupled to the respective medical instruments. The output signals of the medical instruments or of the control apparatuses coupled to them can be transmitted from the central control unit to a central display device. Data or signals can be transmitted from a central input unit to the central control unit, which forwards to one or more control apparatuses or directly to the medical instruments.

The displays or output signals of the medical instruments or the control apparatuses coupled to them can be displayed on a single display device, such as, for example, a flat screen, wherein the displays of the different medical instruments may be displayed in windows assigned to the individual instruments. The images recorded by a laparoscope can, for example, be displayed in a first window, the images recorded by an endoscope displayed in a second window and the data captured by various instruments with respect to the condition of the patient displayed in a third window.

In one embodiment, the outputs or displays of different instruments or apparatuses can be combined, such that, for example, the structure of a body or body part recorded using an imaging method can be displayed in a window and data from other instruments, for example, for navigating, can be superimposed onto this display.

The display of the output information of the different medical instruments can be formed such that a menu function can be realized. It is possible to select from the different instruments coupled to the central control unit via a menu, and in a sub-menu, which then appears, specific to the respective instrument, other adjustments or alterations to a functionality of the instrument can be made.

In the event that particular conditions arise, predetermined beforehand, such as, for example, a critical patient condition or problems with the anaesthesia, an acoustic and/or optical warning signal can be generated, such that, for example, the display of an instrument monitoring the condition of the patient's health is automatically brought to the foreground if the condition of the patient's health changes, due to a significant change in the breathing or heartbeat. This can ensure that critical patient conditions are not inadvertently overlooked due to the multitude of information displayed.

In one embodiment, the environmental conditions of the surgical workstation can also be changed. For example, the brightness or the lighting in general, the volume of acoustic outputs, the temperature or other parameters can be adjusted.

In accordance with another aspect, the invention relates to a computer program or software which, when it is loaded onto a computer or run on a computer, performs one or more of the methods or steps described above.

The invention furthermore relates to a program storage medium or to a computer program product which comprises such a program or software.

BRIEF DESCRIPTION OF THE DRAWINGS

These and further features of the present invention will be apparent with reference to the following description and drawings, wherein.

DETAILED DESCRIPTION OF THE INVENTION

Figure 1:
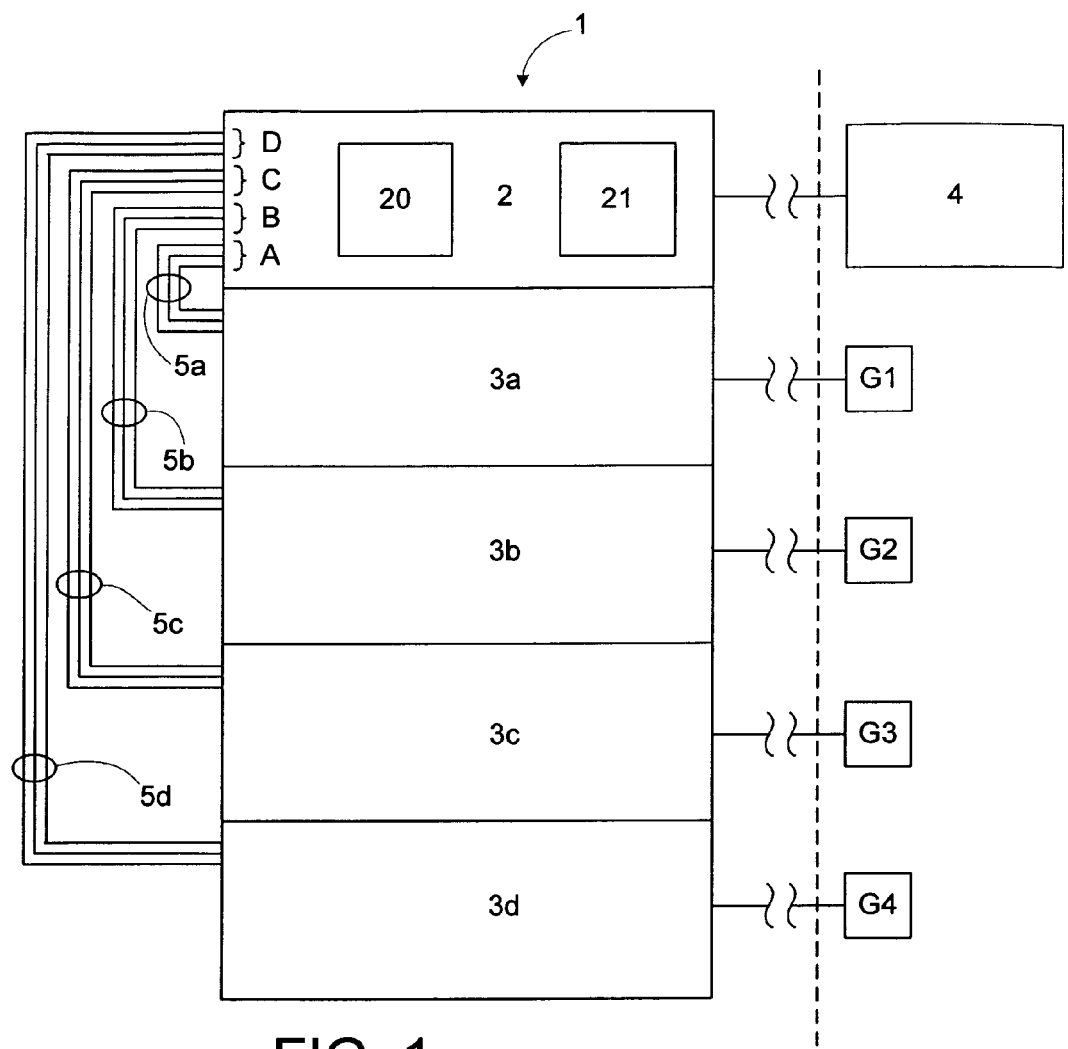
FIG. 1 is a schematic representation of a system in accordance with the invention.

FIG. 1 shows a device 1 in accordance with one embodiment of the invention including a central control unit 2. The central control unit 2 includes the connections indicated by A, B, C and D, to which the lines 5a, 5b, 5c and 5d are connected. The lines 5a, 5b, 5c and 5d couple the central control unit 2 to the control apparatus 3a, 3b, 3c and 3d. The control apparatuses 3a, 3b, 3c and 3d are coupled to medical instruments or apparatuses G1, G2, G3 and G4. Examples of such instruments include, but are not limited to, endoscopes, laparoscopes, a drill apparatus, ultrasound apparatus, infrared apparatus, nuclear spin tomographs, computer tomographs, pumps for medical substances and the like. The control apparatuses 3a-3d can come from various manufacturers and exhibit various operational designs in order to be able to control and operate the medical instruments G1-G4 coupled to them.

The input and output connections on the respective control apparatuses 3a-3d, for example for outputting readings or image signals or for inputting control signals of an externally connectable device for inputting control signals, such as for example a keyboard or a cursor control device, are coupled to the central control unit 2. The central control unit 2 can include at least one processor 20 that can convert output signals of the control apparatuses 3a-3d into a unified format, in order to output them on a single central display unit 4, such as a screen, in parallel or individually, in accordance with a set mode. In the example embodiment, the screen 4 can be formed as a touch screen and can, therefore, also be used for inputting control signals, which are transmitted to the central control unit 2. One or more processors 21 can be provided in the central control unit 2, to convert the control signals coming from the screen 4 into formats corresponding to the respective control apparatus 3a-3d, which can be forwarded to the corresponding control apparatus 3a-3d via the lines 5a-5d. In this way, the central display and control device can serve to operate a multitude of different medical instruments G1-G4.

The broken line shown in FIG. 1 indicates the separation between the device 1 in accordance with the invention and an operating theater or room in which the screen 4, together with the medical electric or electronic instruments G1-G4, are situated. The device 1 can be placed outside the operating theater and, therefore, does not have to fulfil the special medical standards, which apply to apparatuses used in the operating area. Using just one screen 4 to control a multitude of medical instruments makes the operating area easier to survey and thus enables greater freedom of movement as compared to previously known arrangements having a multitude of display devices. In general, instead of the one display device 4 shown by way of example, two or more display devices can also be provided, in order, for example, to also be able to display information to a physician's or surgeon's assistant.

Figure 2:
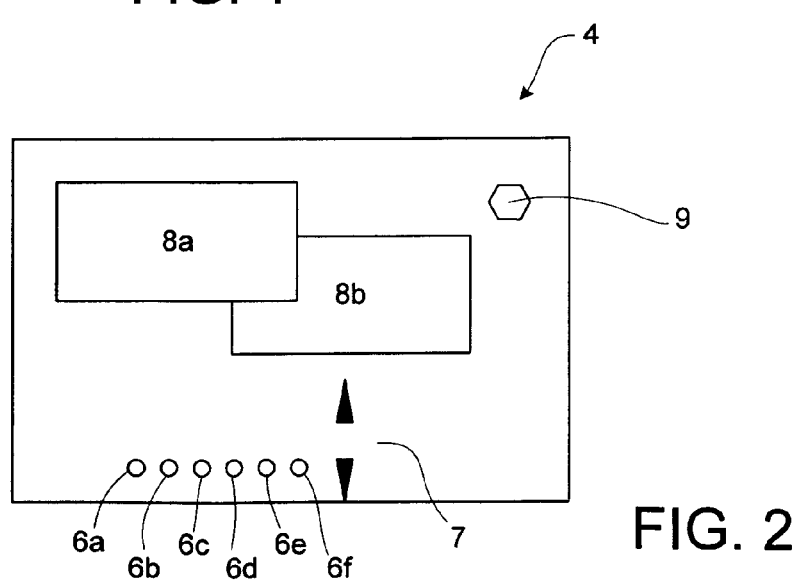
FIG. 2 is a schematic view of a screen output which may be realized using the system in accordance with the invention.

FIG. 2 shows an exemplary display on the display device 4 shown in FIG. 1. The display device 4 can be formed as a touch screen and in the lower area indicates elements 6a-6f via which, for example, the medical instruments G1-G4 or individual menu items of a selected menu can be chosen. The symbols shown by way of example as arrow tips 7 pointing upwards and downwards can be used to "leaf" through a menu, to adjust or change values in order for example to increase or reduce the brightness of a lamp. In the windows 8a and 8b of the screen 4, shown by way of example, the video images from two different cameras can be displayed, wherein, for example, one or more windows can be opened for each individual medical instrument. Displaying a multitude of different programs and information using windows that can overlap on the screen is known in the prior art and accordingly will not be described in more detail here.

An alarm display 9 is provided at a fixed position on the display device 4, wherein the display 4 can be controlled such that the alarm display 9 cannot be covered by windows 8a or 8b. The alarm display 9 can, for example, output an easily detected blinking signal, if it is established via one of the medical instruments G1-G4 that the patient's condition has changed or is critical.

Although particular embodiments of the invention have been described in detail, it is understood that the invention is not limited correspondingly in scope, but includes all changes, modifications and equivalents coming within the spirit and terms of the claims appended hereto.

What is claimed is:

1. A system comprising:
   a central control unit configured to couple to input and output connections of at least two medically applicable instruments via at least two control apparatuses having different manufacturer-specific command protocols and associated command protocol software; and
   a common output display device coupled to the central control unit via a bus, wherein the bus provides electrical separation between the common output display device and the central control unit;
   at least one input device coupled to the central control unit and configured to receive operator input;
   wherein the central control unit is configured to receive output signals from the at least two control apparatuses and adapt the received output signals for display on the common output display device, and the central control unit is configured to receive input signals from the at least one input device and relay the received input signals to the at least two control apparatuses; and
   wherein the central control unit is configured to receive output signals and relay received input signals without conversion of the received input signals to command protocols of the least two medically applicable apparatuses.

2. The system as set forth in claim 1, wherein the common output display device is a single central input and output display device comprised of a single touch screen display.

* * * * *